United States Patent
Cranley et al.

(10) Patent No.: US 6,609,068 B2
(45) Date of Patent: Aug. 19, 2003

(54) PERSONAL COMPUTER BREATH ANALYZER FOR HEALTH-RELATED BEHAVIOR MODIFICATION AND METHOD

(75) Inventors: Paul E. Cranley, Lake Jackson, TX (US); James D. Tate, Lake Jackson, TX (US); Ted E. Miller, Midland, MI (US); Alan D. Strickland, Lake Jackson, TX (US); Charles J. McDonald, Midland, MI (US); Michael J. Bartels, Midland, MI (US); Alan K. Schrock, Lake Jackson, TX (US); Scott P. Crane, San Diego, CA (US)

(73) Assignee: Dow Global Technologies Inc., Midland, MI (US)

( * ) Notice: Subject to any disclaimer, the term of this patent is extended or adjusted under 35 U.S.C. 154(b) by 110 days.

(21) Appl. No.: 09/799,402

(22) Filed: Mar. 5, 2001

(65) Prior Publication Data

US 2002/0007249 A1 Jan. 17, 2002

Related U.S. Application Data

(63) Continuation-in-part of application No. 09/779,160, filed on Feb. 8, 2001.
(60) Provisional application No. 60/184,039, filed on Feb. 22, 2000.

(51) Int. Cl.$^7$ .......................... G06F 19/00; G01N 31/00
(52) U.S. Cl. ..................................................... 702/24
(58) Field of Search ............................ 702/24; 600/529, 600/409, 484; 128/204, 205, 923; 180/272; 422/84; 250/339.03

(56) References Cited

U.S. PATENT DOCUMENTS 4,114,422 A    9/1978   Hutson .................. 73/23.1

(List continued on next page.)

FOREIGN PATENT DOCUMENTS

EP    0 556 614 A1    1/1993

(List continued on next page.)

OTHER PUBLICATIONS

Patent Abstract of Japan, Publication No. 2001–349888, Dec. 21, 2001 (English translation of JP 2001–349888).

(List continued on next page.)

*Primary Examiner*—John Barlow
*Assistant Examiner*—Aditya S. Bhat

(57) ABSTRACT

A medical breath component analyzer which maintains a data-base profile of a patient over time. The apparatus may be used chronically by a patient so that a baseline status for that patient may be determined. Acute variations from the baseline are identified as clinically significant. The acquired data can be reported to the patient using the device at home and transmitted electronically to a physician or health care provider. The method and apparatus helps a patient modify health related behaviors, particularly weight loss for diabetic patients. A breath component and information on the psychological or emotional state of the patient are correlated, and information is provided to the patient based on the correlation between the breath component and the patient's emotional state. Other physiologic parameter may also be measured, such as a blood component, temperature, cardiovascular condition or pulse rate, a urine component, a physical activity sensor, weight, or body fat composition sensor. The parameters and the information on the patient's emotional state may be correlated through a computer system. Correlation may comprise selecting a response likely to re-enforce positive behavioral change in the patient. Preferably, remote sources of information may also be accessed, as, for example, through a communications connection or the Internet. Information may be provided directly from the apparatus, or by contact through a physician, health-care provider or support group.

58 Claims, 8 Drawing Sheets

U.S. PATENT DOCUMENTS

| | | | | |
|---|---|---|---|---|
| 4,258,718 A | * | 3/1981 | Goldman | 600/409 |
| 4,440,177 A | * | 4/1984 | Anderson et al. | 128/205.12 |
| 4,463,764 A | * | 8/1984 | Anderson et al. | 600/484 |
| 4,809,810 A | * | 3/1989 | Elfman et al. | 180/272 |
| 4,970,172 A | * | 11/1990 | Kundu | 128/205.12 |
| 5,071,769 A | * | 12/1991 | Kundu et al. | 382/115 |
| 5,174,959 A | * | 12/1992 | Kundu et al. | 600/529 |
| 5,260,219 A | | 11/1993 | Fritz | 436/71 |
| 5,303,575 A | * | 4/1994 | Brown et al. | 422/84 |
| 5,422,485 A | | 6/1995 | Bowlds | 250/343 |
| 5,426,415 A | * | 6/1995 | Prachar et al. | 340/576 |
| 5,515,859 A | | 5/1996 | Paz | 128/719 |
| 5,543,621 A | | 8/1996 | Sauke et al. | 250/339.03 |
| 5,592,402 A | | 1/1997 | Beebe et al. | 364/578 |
| 5,640,014 A | | 6/1997 | Sauke et al. | 250/339.03 |
| 5,691,701 A | * | 11/1997 | Wohlstein et al. | 340/603 |
| 5,721,142 A | * | 2/1998 | Klemm et al. | 128/204.18 |
| 5,876,926 A | * | 3/1999 | Beecham | 382/115 |
| 5,971,934 A | * | 10/1999 | Scherer et al. | 128/923 |
| 6,039,923 A | * | 3/2000 | Klemm et al. | 340/576 |
| 6,192,876 B1 | * | 2/2001 | Denyer et al. | 128/204.18 |
| 6,248,078 B1 | * | 6/2001 | Risby et al. | 600/529 |
| 6,479,019 B1 | * | 11/2002 | Goldstein et al. | 600/409 |
| 2003/0008407 A1 | | 1/2003 | Fu | |

FOREIGN PATENT DOCUMENTS

| | | | | |
|---|---|---|---|---|
| EP | 647427 A1 | * | 5/1994 | A61B/5/08 |
| EP | 0 279 069 B1 | | 7/1994 | |
| EP | 1 167 971 A2 | | 1/2002 | |
| GB | 2 218 514 A | | 11/1989 | |
| JP | 2000005145 A | * | 6/1998 | A61M/16/00 |
| JP | 2001-349888 | | 12/2001 | |
| WO | WO 98/29563 | | 7/1998 | |
| WO | WO 98/39470 | | 9/1998 | |
| WO | 98/53732 | | 12/1998 | |
| WO | 99/66304 | | 12/1999 | |

OTHER PUBLICATIONS

"Gas Analysis System for Medical Diagnosis Used as Electronic Nose", DERWENT (DE 29902593).

Phillip, Michael et al., "Variation in volatile organic compounds in the breath of normal humans," Journal of Chromatography B, vol. 729, pp. 75–88 (1999).

Manolis, Antony, "The Diagnostic Potential of Breath Analysis," Clinical Chemistry, vol. 29, No. 1, pp. 5–15 (1983).

Mitsubayashi, Kohji et al., "Gas–Phase Biosensor for Ethanol," Research Center for Advanced Science and Technology, vol. 66, No. 20 (1994).

Moskalenko, Konstantin L. et al., "Human breath trace gas content study by tunable diode laser spectroscopy technique", Infrared Physics and Technology, vol. 37, No. 1, pp. 181–192 (1996).

Paldus, B. A. et al., "Absorption Spectroscopies: From Early Beginnings to Cavity–Ringdown Spectroscopy", Acs. Symp. Ser., pp. 49–70 (1999).

Park, Je–Kyun et al., "Determination of breath alcohol using a differential–type amperomatic biosensor based on alcohol dehydrogenase", Analytica Chimica Acta, vol. 390, pp. 83–91 (1999).

Phillips, Michael, "Breath Tests in Medicine", Scientific American, pp. 74–79 (1992).

Reichard, G. A., et al., "Plasma Acetone Metabolism in the Fasting Human", J. Clinic. Invest., pp. 619–626 (1979).

Rooth, Gösta et al., "Acetone in Alveolar Air, and the Control of Diabetes", The Lancet, pp. 1102–1105 (1966).

Yamamoto, Hiroshi et al., "A breath ketone determination method as a noninvasive test for the metabolic indicator in diabetes and obesity", Int. Congr. Ser., pp. 617–621 (1995).

Cheng, Wu–Hsun et al., "Technical development in breath micoanalysis for clinical diagnosis," J. Lab Clin. Med., pp. 218–228 (1999).

Chiarelli, Fransesco et al., "Modern management of childhood diabetes: A role of computerized Devices?", Acta Paediatrica Japonica, vol. 40, pp. 299–302 (1998).

Crofford, Oscar B. et al., "Acetone in Breath and Blood", Trans. Am. Clinic. Climat. Assoc., pp. 128–139 (1977).

Crofford, Oscar B., "Adult Diabetes", Sugars Nutr, pp. 513–524 (1974).

Ivanov, Sergey V. et al., "Laser infrared spectrometer for atmosphere gas analysis and medicine", Optical Engineering, vol. 33, No. 10, pp. 3202–3204 (1994).

Jones, A.W., "Breath Acetone Concentrations in Fasting Healthy Men: Response of Infrared Breath–Alcohol Analyzers", Journal of Analytical Toxicology, vol. 11, No. 2, pp. 67–69 (1987).

* cited by examiner

| FIG. 3A | FIG. 3B |
|---|---|
| | FIG. 3C |

Fig. 3

PERSONAL COMPUTER BREATH ANALYZER FOR HEALTH-RELATED BEHAVIOR MODIFICATION AND METHOD

Thi application is a continuation-in-part of U.S. Ser. No. 09/779,160 filed Feb. 28, 2001, which claims the benefit of provisional application 60/184,039 filed Feb. 22, 2000.

FIELD OF THE INVENTION

This invention relates generally to methods and medical apparatus and in particular to methods and apparatus for modifying health-related behavior, such as weight control for diabetes or general health. More particularly the invention relates to apparatus for analyzing medically significant components in exhaled breath.

BACKGROUND ART

Diabetes is a chronic disease affecting many organs and body functions. The disease is caused either by a lack of the hormone insulin or by the body's inability to use insulin. Diabetes is the most common endocrine disorder. In the United States, for instance, as many as 10 million persons have diagnosed diabetes mellitus, and it has been estimated that an additional 10 million may have the disease without diagnosis. Although there is no cure, most cases can now be controlled adequately by a combination of medication and life style modification, including exercise, diet and weight loss.

Unfortunately, many people with diabetes have difficulty coping with the constraints that the disease puts on their lives. People find it difficult to lose weight, to maintain weight loss, to exercise regularly, to regularly take drugs, or to self-administer tests for blood glucose levels. In general, patients do not receive sufficient positive support for their efforts and can become discouraged. They experience "diabetes burn-out", a feeling of hopelessness or powerlessness that contributes to abandoning efforts to manage their disease. People who are simply overweight or obese can experience similar barriers when attempting to control their diet and weight. See, for example, *Diabetes Burnout, What to Do When You Can't Take It Anymore,* W. H. Polonsky, 1999, American Diabetes Association.

Weight loss is particularly difficult to sustain. Preferably, for weight loss, caloric intake should be reduced to produce an energy deficit of about 500 Calories daily, which usually results in the loss of about one pound of body weight per week. Experts frequently recommend that the body weight be monitored weekly during the process of weight loss. Daily variation in water content of the body and lack of sensitivity of most scales tend to mask any true change. Moreover, contemporaneous improvement in muscle tone from exercise may actually produce an initial increase in weight. Consequently, a weight reduction diet may produce the desired results very slowly, and progress may be hard to measure. Many people, by contrast, expect rapid, dramatic changes in their condition. Still others expect failure and find this belief confirmed by the slow rate of change in their health. An accurate, rapid feedback mechanism is needed to help patients sustain changes in life style which will lead to sustained weight loss.

It is known that a person exhales acetone in the breath when the body is in a condition of energy deficit, that is, when the body is using more energy than it is taking in through food or beverages. Ketosis is, therefore, an immediate measurable indication that a person is successfully maintaining a reducing diet. See, for example, Samar K. Kundu et al., "Breath Acetone Analyzer: Diagnostic Tool to Monitor Dietary Fat Loss", Clin. Chem., Vol. 39, No. 1, pp.87–92 (1993).

The potential for the use of exhaled breath as a diagnostic tool has long been recognized. Hippocrates taught the physician to be aware of the smell of the patient's breath, as a clue to the patient's condition. In 1784 Antoine Lavoisier and Pierre Laplace analyzed breath of a guinea pig, finding that an animal inhales oxygen and exhales carbon dioxide. This was the first direct evidence that the body uses a combustion process to obtain energy from food. Since that time, as many as 200 compounds have been detected in human breath, some of which have been correlated with various diseases.

Detection apparatus for breath components employ varying technologies. Infrared light has been used to measure breath alcohol content by Bowlds U.S. Pat. No. 5,422,485 and Paz U.S. Pat. No. 5,515,859. Sauke et al. U.S. Pat. No. 5,543,621 used a laser diode spectrometer. Other types of lasers and absorption spectroscopes have been used including cavity-ringdown spectroscopy. See, e.g. "Absorption Spectroscopes: From Early Beginnings to Cavity-Ringdown Spectroscopy" B. A. Paldus and R. N. Zare, American Chemical Society Symp. Ser. (1999), Number 720, pp. 49–70. Other techniques include gas-liquid chromatography ("GC"), mass spectrometry, coupled GC-Mass Spectroscopy, electrochemistry, colorimetry, chemiluminescence, gas biosensors, and chemical methods. See, e.g., "The Diagnostic Potential of Breath Analysis", Antony Manolis, Clinical Chemistry, 29/1 (1983) pp. 5–15, and "Technology Development in Breath Microanalysis for Clinical Diagnosis", Wu-Hsum Cheng, et al., J. of Laboratory and Clinical Medicine, 133 (3) 218–228 March, 1999. Among the chemical sensors are so-called electronic noses, which rely on an array of detectors to recognize patterns of physical or chemical characteristics to identify components. These sensors may rely, for example, on conductive polymers, surface acoustical wave generators, metal oxide semiconductors, fluorescence or electrochemical detection. Such sensors are commercially available from Cyrano Sciences, Pasadena, Calif., for example, and their use in detecting medical conditions such as pneumonia, halitosis and malignant melanoma has been suggested.

Many of these technologies are complex, expensive and difficult to calibrate. They have not been economically adapted for individual health care use. It has been suggested, however, that self-administered breath alcohol tests could be used (See, Brown et al. U.S. Pat. No. 5,303,575) by multiple individuals at bars or other locations where alcoholic beverages are served to detect a predetermined level of breath alcohol.

SUMMARY OF THE INVENTION

We have invented a method and apparatus for helping a patient modify health related behaviors, particularly weight loss and more particularly weight loss for diabetic patients. The method comprises measuring a physiologic parameter correlated to the behavior or condition to be changed, obtaining information on the psychological or emotional state of the patient, correlating the parameter and the information so measured or obtained, and providing information to the patient based on the correlation between said parameter and said state. The physiologic parameter may be a blood component, temperature; cardiovascular condition or pulse rate, a urine component, a physical activity sensor, weight, body fat composition sensor, or a component of the exhaled breath. Preferably the parameter can be measured non-invasively. Most preferably, the parameter is a component of the exhaled breath, in particular, acetone. Information on the psychological or emotional state of the patient may be obtained interactively through a self-administered computer-based questionnaire and may include correlation with past answers to questions, elapsed time in treatment, or trends in the information. The parameter and the information may be correlated through a computer system. Correlation may comprise selecting a response likely to re-enforce positive behavioral change in the patient. Preferably, remote sources of information may also be accessed, as, for example, through a communications connection. An example of such a connection may be an interactive connection to the Internet. Information may be provided directly from the apparatus, or by contact through a physician, health-care provider or support group.

Measuring acetone in exhaled breath to detect a condition of energy deficit presents certain difficulties. The preferred rate of energy deficit is about 500 Calories per day. This is a lower rate than used in ultra-low calorie diets under controlled clinical conditions. Consequently, low levels of exhaled acetone may be expected. Moreover, metabolic rates may vary among persons because of fitness or general state of health, including the progress of a disease such as diabetes. To overcome the difficulties of calibration, patient-to-patient variation, and other problems, we have invented a medical breath-component analyzer, which maintains a database profile of a patient over time. It is intended that a patient use our invention over an extended period so that a baseline status for that patient may be determined. Acute variations from baseline are identified as clinically significant. The acquired data can be reported to the patient using the device at home and transmitted electronically to a physician or health care provider. Alternatively, the data may be maintained at a remote location, such as a website, and accessed by the physician or health care provider as needed. Multiple tests may be provided, including quantitative tests, qualitative tests, and quantitative approximations using qualitative devices. In particular, laser spectroscopy with multiple lasers having different output characteristics may be used on a single breath sample. The merged output of the plurality of lasers can form a template or pattern, characteristic of a particular patient, whereby complex conditions may be more easily recognized. A set of tests is selected for a particular patient, and may be customized to the patient's condition. If a change in condition is detected, additional environmental and user-supplied information may be acquired to determine if a change is clinically significant.

BRIEF DESCRIPTION OF THE DRAWINGS

FIG. 3 is a drawing showing the relationship of FIG. 3A, FIG. 3B and FIG. 3C.

DETAILED DESCRIPTION OF THE PREFERRED EMBODIMENT

Figure 1:
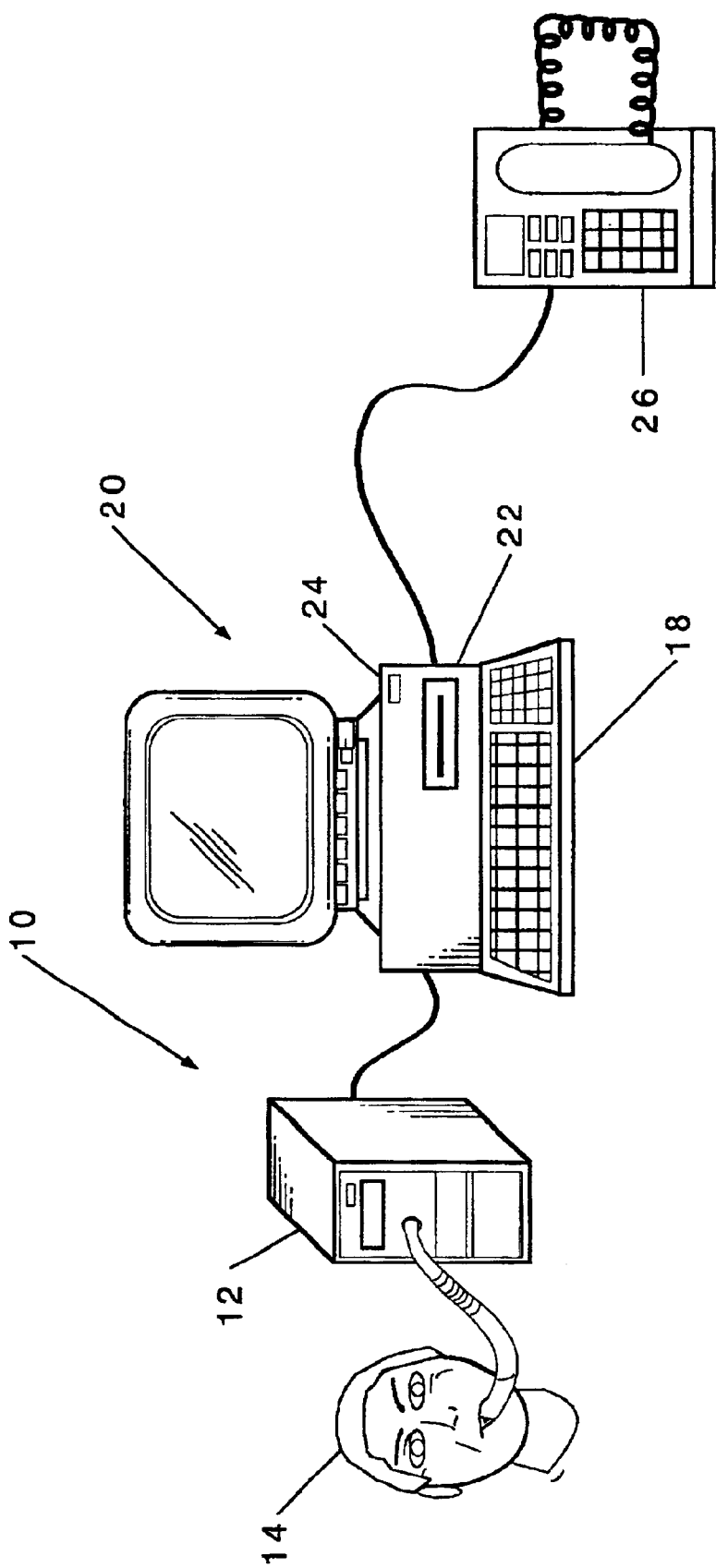
FIG. 1 is a perspective drawing of a diagnostic breath analysis system according to the present invention.

We will now describe our invention in connection with the accompanying figures, wherein like numerals are used to designate like parts in each drawing. FIG. 1 illustrates a diagnostic breath analysis system 10 according to our invention. The system comprises an analysis unit 12, which receives a breath sample from a patient 14 and provides quantitative and qualitative analysis of that sample as will be more fully explained below. Analysis of breath samples for diagnostic purposes has the advantage that the sample is collected non-invasively with a minimum of discomfort or inconvenience. The data resulting from the analysis is transferred to and stored in a computer 16, preferably a microcomputer having an input device or devices 18, such as a keyboard or mouse, an output device 20 such as a video monitor, printer, or other means of displaying data, memory 22 and an appropriate CPU 24. The computer 16 is preferably connected to an information grid 26 such as a telephone system or the Internet. The data may optionally be stored in a remote database via a phone or Internet connection. Alternatively, the data may be transmitted using wireless means to allow the analysis unit 12 to be portable for use at work, etc.

Figure 2:
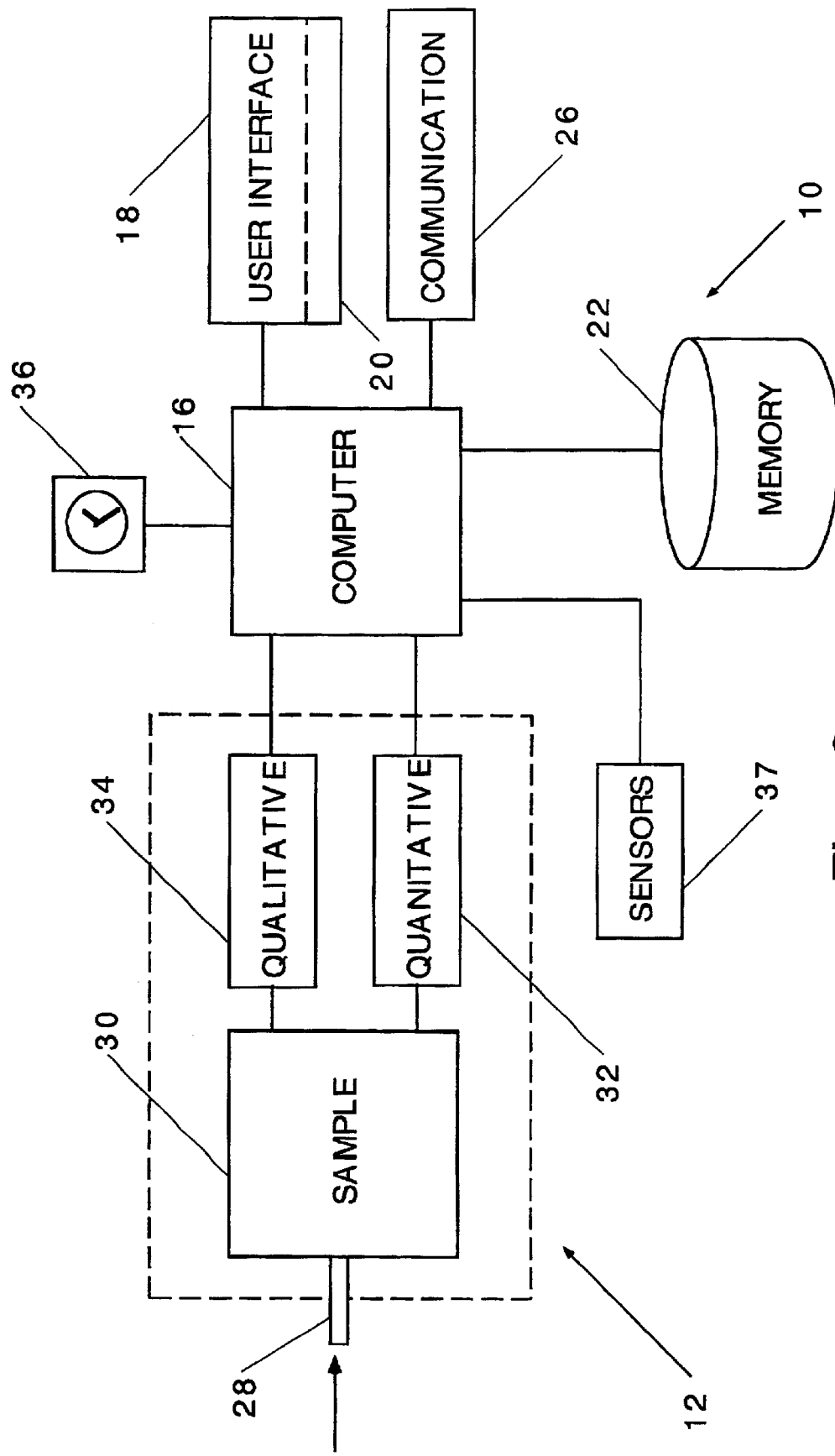
FIG. 2 is a block diagram of the system of FIG. 1.

The basic components of the breath analysis system 10 can be further understood with reference to FIG. 2. The breath analyzer 12 comprises a mouthpiece 28 connected to a sampling device 30. The sampling device 30 captures a portion of the patient's exhaled breath, preferably alveolar breath from deep within the lungs. The first part of exhaled breath usually contains "dead space" air, that is, air from the upper airways such as the trachea, mouth and nasal cavities. Dead space air does not contain many of the components that are of interest in making a diagnosis. In general, the first 150 ml of expiration is dead space air. About 500 ml is exhaled in each breath. About ninety percent of the breath is nitrogen and oxygen. The breath sample may be captured in a chamber or in a trap or both, depending on the apparatus employed for qualitative and quantitative analysis of the sample. Generally, traps fall into three categories: chemical, cryogenic, and adsorptive.

It is important that the sample be representative of the breath of the user, and not contaminated by other influences. One approach is to inhale the air through the device to obtain a background value that will then be automatically subtracted from the exhaled value. The system 10 should also be calibrated from time to time. This may be done by injecting a gas of known composition into the sampling device. A gas-filled canister may be provided for this purpose. It is also important to purge the sampling device after use to discharge excess moisture or other components. This can also be accomplished by the injection of a gas and the two functions of calibration and purging may be performed in a single step. Certain types of analyzers are more stable and require less calibration than others. Cavity ring-down spectroscopy, for example, may require reference or "zero" calibration, but will remain stable unless the associated laser or cavity is changed.

Although calibration is important, our invention reduces reliance on absolute standards by maintaining the patient profile or history. Thus a particular patient will usually be able to provide a consistent volume of breath for a sample. The volume will vary from patient to patient, but because records are maintained for the patient, the criticality of sample volume and other repetitive or consistent background factors (for example, air quality) is reduced or removed. Such features contribute to the usefulness of the apparatus in, for example, individual homes where each family member would develop their own profile by entering identifying information into the computer in connection with providing a sample.

Certain portions of the sample are processed in a quantitative analyzer 32. Quantitative analyzers may include laser spectroscopic devices, gas-liquid chromatography (GC), mass spectrometry, coupled GC-mass spectroscopy, electrochemistry, colorimetry, chemi-luminescence, gas biosensors and chemical methods and even certain electronic nose sensor arrays capable of performing quantitative measurements. Electronic nose sensor systems may be based on an array of several different types of solid state sensor elements. Among the most sensitive are polymer-coated surface acoustic wave ("SAW") oscillators that operate in the 100 megahertz range. Each element can easily sense as little as a femtogram ($10^{-15}$ gram) of absorbed mass. Upon exposure to vapor-phase samples, patterns of change in the masses of these elements are than seen as frequency shifts and interpreted by signal processing networks. These "neural networks" are computational layers of signal processing that compare these patterns to known responses characteristic of the target vapors "learned" in prior exposures to known compounds. The system then reports the result, usually along with statistical significance, or probability of correctness. The advantages of the electronic nose sensor include compactness and low cost due to an absence of moving parts. Improvements in on-chip memory capacities and signal processing speeds contribute to the usefulness of electronic nose sensor arrays for tracking vapors.

A qualitative analyzer 34 may also be provided. These analyzers may be better at recognizing the presence of specific compounds than they are at measuring the concentration of the compound. Electronic nose sensor arrays may be also used in a qualitative configuration. Other possibilities include ion mobility spectrometer detectors, quadruple mass spectrometer detectors, enzyme based microcalorimetry or electrochemical detectors and their arrays, and fiber optic detectors and their arrays. Processed data from both the quantitative analyzer 32 and the qualitative analyzer 34 are stored in memory 22 of the computer 16 or alternatively on a remote database accessible by phone or web connection. Preferably both quantitative and qualitative analyzers may be based on solid-state technology with consideration for reliability, accuracy and cost.

In our invention, data from a particular patient is stored so that multiple samples over an extended period of time may be taken. This permits a baseline to be established for a particular patient, and trend analysis can be performed on the resulting data. If there is an acute and significant change in the chronic condition of the patient's breath, indications of this change may be sent by communications 26 to a physician or healthcare provider. It is important, therefore, that the patient 14 be identified through the user interface such as the keyboard 18. Identification may alternatively be verified by pattern recognition of breath components, voice, fingerprint, and photographic or other similar input from the patient. Moreover, a clock 36 should be provided and connected to the computer 16. Quartz crystal-based real-time clocks are common features of personal computers. The computer 16 should distinguish between multiple samples taken during a single session of data acquisition and multiple sessions of data acquisition that occur over an extended period of time, for instance, days, weeks, or months. The rate of change of the components of the breath over time is important in determining if a change in the patient's health, diet, or other condition has occurred. Additional sensors 37 may also be provided. These sensors may include an environmental thermometer, a barometer, a hygrometer, or other sensors for determining the condition in which the sample is given. The sensors may also include additional patient sensors, such as a patient thermometer, heart rate or blood pressure sensors. Another sensor might be a camera or voice recognition device to confirm the patient's identity as well as to record more information on the patient's health. The output from the sensors 37 would be stored with the data obtained from the breath analysis and might also be used to determine if a particular change in breath components were significant or not.

Figure 3A:
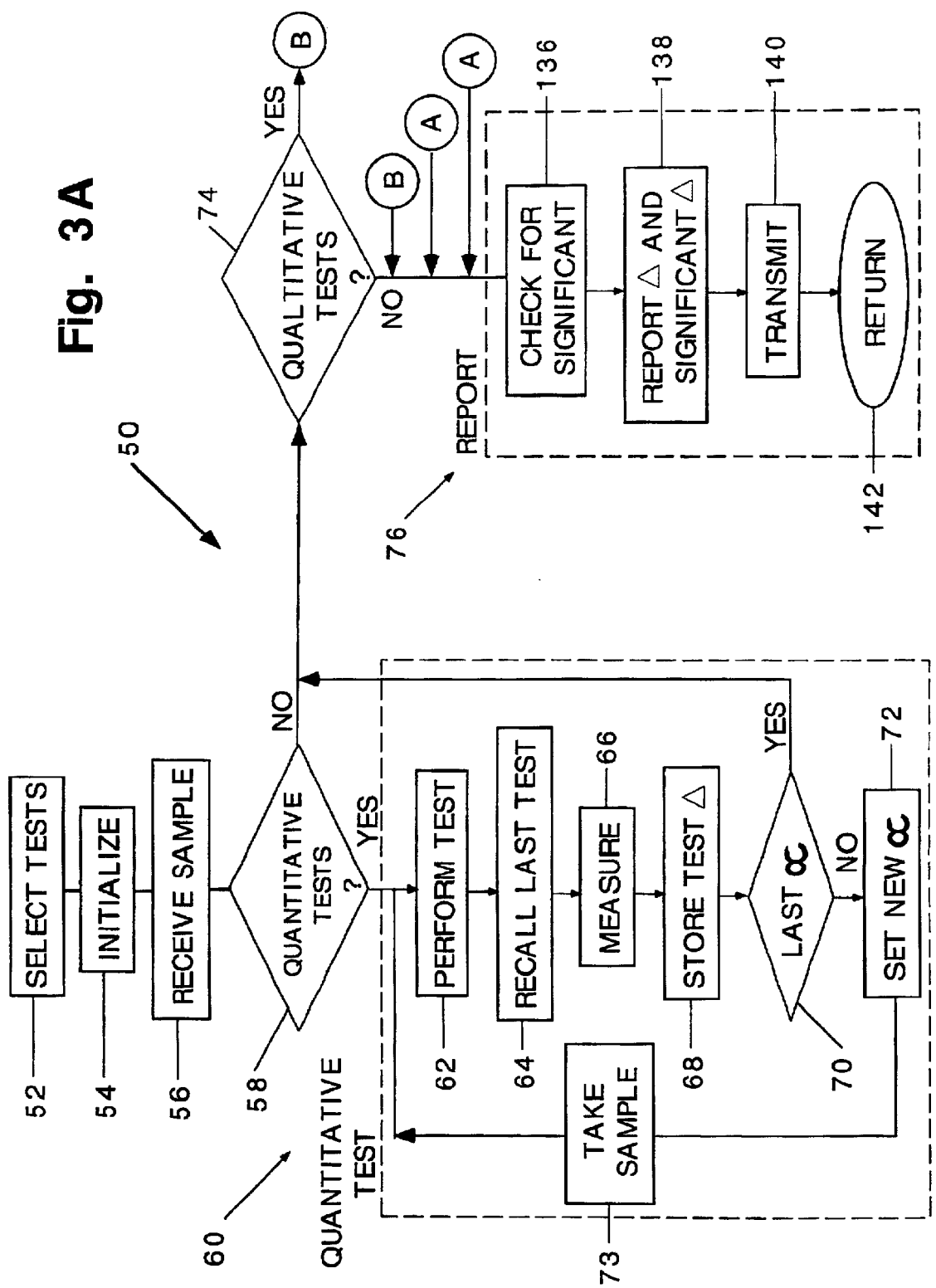
FIG. 3A is a portion of a flowchart for the system of FIG. 1.
Figure 3B:
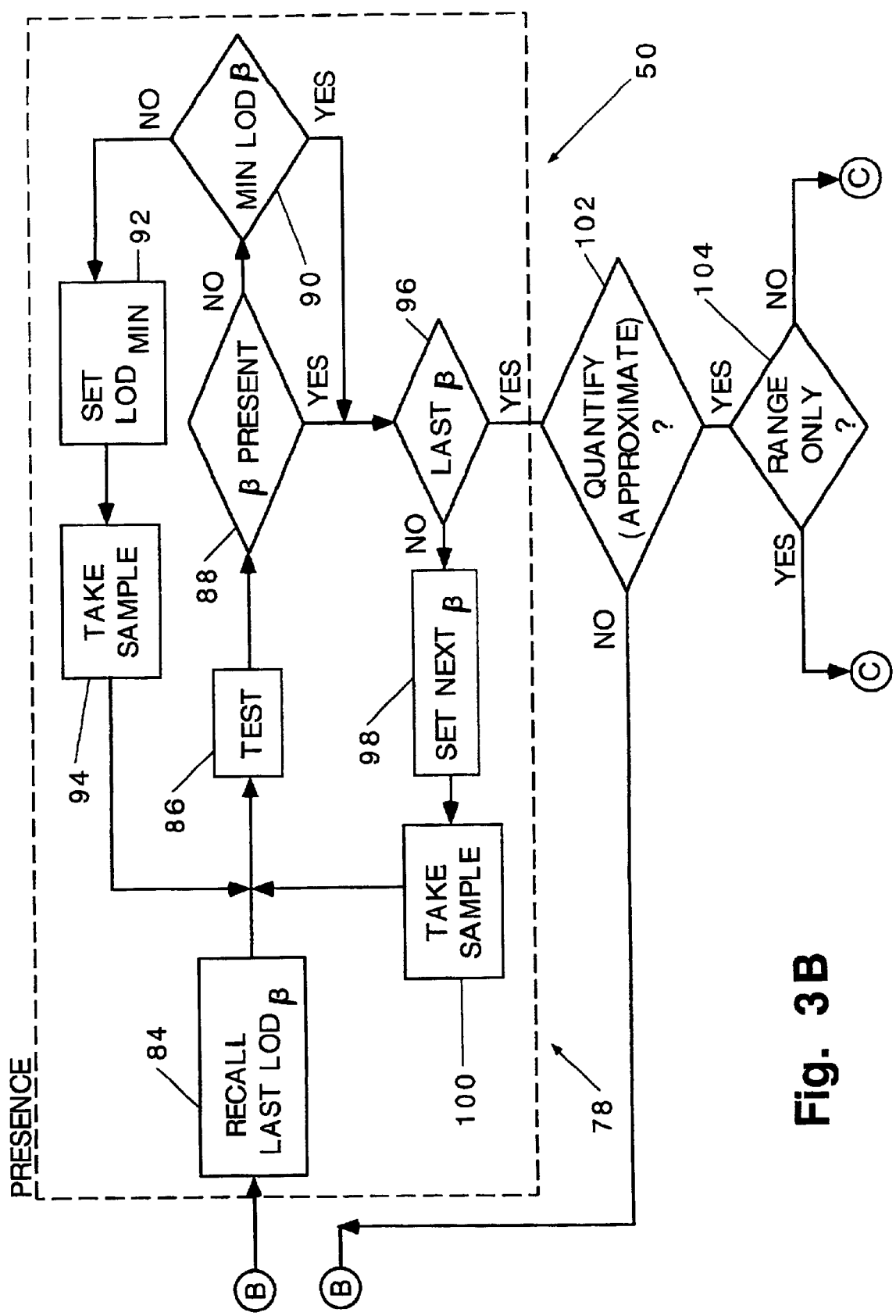
FIG. 3B is an additional portion of the flowchart for the system of FIG. 1.
Figure 3C:
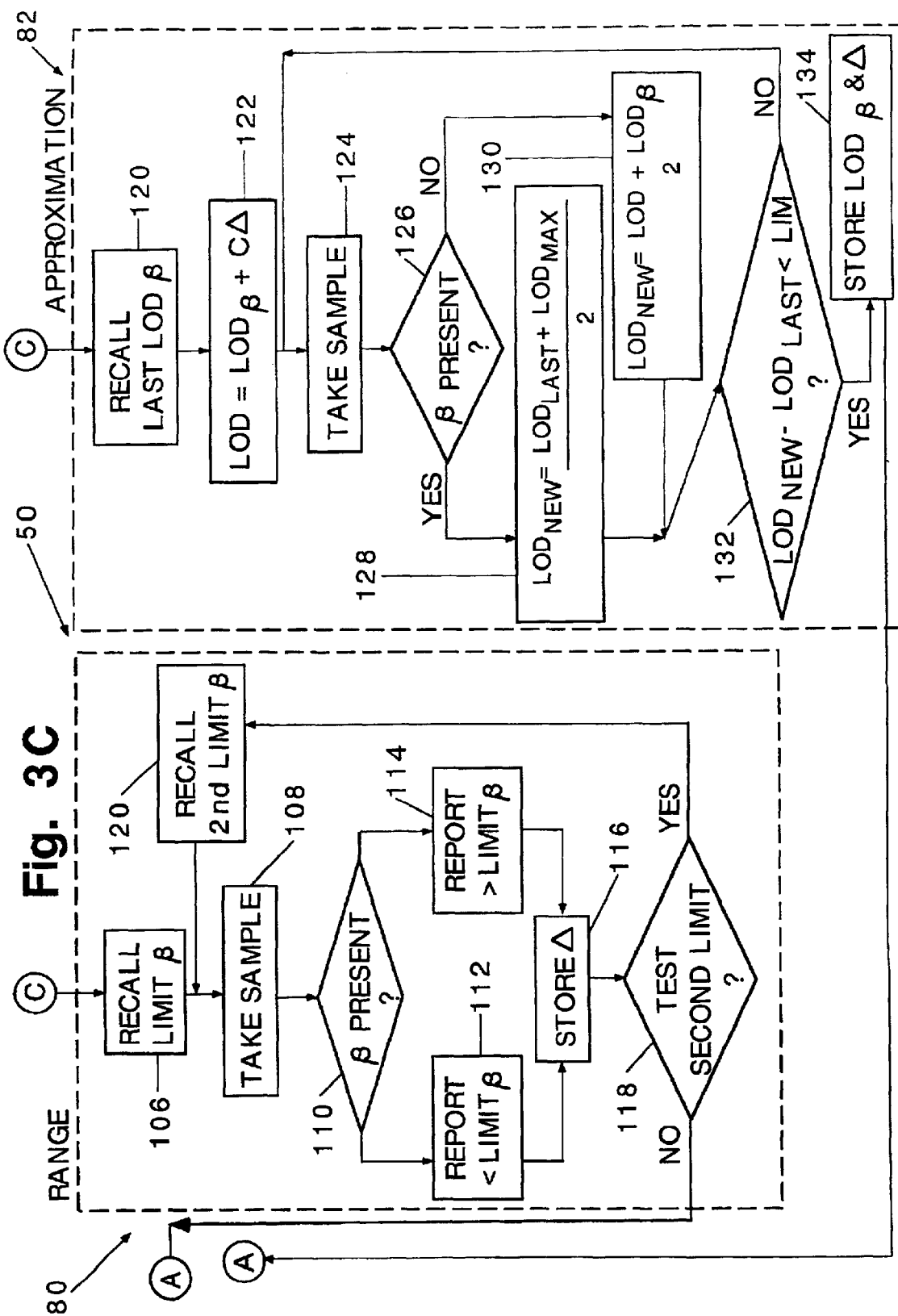
FIG. 3C is a final portion of the flowchart for the system of FIG. 1.

Processing of the sample by the analysis unit 12 and the computer 16 can be further understood in connection with the flowchart as illustrated in FIGS. 3A, 3B, and 3C. FIG. 3 shows the relationship of FIGS. 3A, 3B, and 3C to each other. The combined figures illustrate a process system 50 for analyzing a patient's breath. Initially, the system 50 should be customized for the particular patient by selecting the tests 52 to be employed, as shown in FIG. 3A. Tests may also be added to or removed from the profile for a particular patient at any time during the use of the apparatus, particularly in response to changes in the patient's condition or for other reasons. The types of tests that may be employed include carbon dioxide content, breath temperature, alcohol, lipid degradation products, aromatic compounds, thio compounds, ammonia and amines or halogenated compounds. As an example of the usefulness of detecting these components, lipid degradation products such as breath acetone are useful in monitoring weight loss, diabetes management, and ovulation. Thio compounds such as methanethiol, ethanethiol, or dimethyl sulfides have diagnostic significance in the detecting widely differing conditions, such as psoriasis and ovulation. Increased ammonia has been associated with hepatic disease. Halogenated compounds may be indicative of environmental or industrial pollutants.

Another set of tests may be based on analysis of certain breath components after the patient has taken a diagnostic reagent, in accordance with instructions from a physician. For example, urea, especially $C^{13}$ labeled urea, or $C^{13}$ labeled carbohydrates may be taken orally and the $C^{13}$-based $CO_2$ analyzed in the exhaled breath to determine if the patient has heliobactor pylori infection of the stomach lining (urea→$NH_3$ and $CO_2$) or carbohydrate malabsorbtion, glucose intolerance, lactase deficiency or small bowel bacterial overgrowth. Carbon 13 isotopes can be differentiated by laser spectroscopy. See, e.g., GB 2,218,514. As explained hereafter (step 140), the resulting data would be transmitted to the attending physician for appropriate action.

Another set of tests could be used to verify and measure the consumption of prescribed foodstuffs and pharmaceuticals by the patient, or to verify the non-consumption of certain substances such as alcohol or illegal drugs.

With particular tests selected for the patient, the system would be initialized 54 to begin to build a baseline or chronic breath condition history for a particular patient. Both during initialization and thereafter, as tests are taken over an extended period of time, a sample would be received from the patient at step 56. The microprocessor 16 determines if quantitative tests 58 have been selected for this particular patient. If quantitative tests have been selected, a quantitative test segment 60 would be performed. Quantitative tests are performed for selected components α, either simultaneously or serially, depending on the capacity of the quantitative test device 32. The tests would be performed 62 using a suitable quantitative device 32, as mentioned above, including, for instance, laser spectroscopic, gas-liquid chromatographic (GC), mass spectrometric, coupled GC-mass spectrometric, electrochemical, calorimetric, chemiluminescent, gas biosensor, and chemical method based devices, certain electronic nose sensor arrays, or other quantitative apparatus. The last stored or baseline test data 64 would then be recalled from memory and the change or delta information between the new test data and stored test data is determined 66. New test data and delta information 68 is stored in memory 22. It is determined at step 70 if the tested component α is the last component for which quantitative tests have been selected. If it is not the last component or α, a new α is set at step 72 and tests for the next component α are then performed. This may be done simultaneously or serially on a single sample if the quantitative device 32 is capable of multiple analysis or an additional sample may be requested of the patient at step 73. Cavity-ring-down laser spectroscopy, for example, is capable of measuring multiple components simultaneously. If the last quantitative test has been performed, control of the device inquires at step 74 whether any qualitative tests should be performed.

If no qualitative tests are to be performed, data would be reported through a report process 76, as will be more fully described below. If qualitative tests are to be performed, the tests may fall into three different types. First, the presence 78 of the breath component alone may be significant to the health of the patient. See FIG. 3B. This may particularly be important where the chronic monitoring of the breath components of the patient have indicated the absence of a component and that component appears in a new test. The converse change may also be significant, that is, if a component formerly present is absent in the new test. Both conditions can be detected by a device because of the maintenance of a patient's specific data history in memory 22.

Second, it may be significant that a newly detected component falls within a given range 80. See FIG. 3C. Although the components may be detected by a qualitative device 34, estimates of the range may be obtained by certain manipulations of the qualitative device. This may be important where it is economically infeasible to employ a quantitative device with respect to a particular component but an approximation can be obtained which is sufficient to alert an attending physician of the need for a more detailed analysis or which is sufficient to allow the patient to follow a course of treatment, as in diet control, either for weight loss or for diabetes.

Third, a more specific approximation 82 may be obtained using the qualitative device as will be more particularly described below. See FIG. 3C. The results of both testing for presence, range and approximation, together with quantitative results would then be reported 76.

Referring now to FIG. 3B, the presence of 78 of a component β may be tested with a qualitative device, for example, an electronic nose sensor array, by recalling 84 the patient's last settings for detection of the desired components at a level of detection ("LOD β") for that particular component. Qualitative tests would then be performed at 86. At step 88, it is determined if the component β is present. If the test for component β is negative, it should be determined 90 if the minimum or most sensitive setting for the LOD β has been used. If greater sensitivity can be employed, the sensitivity would be adjusted 92 to maximum or LOD min and, if necessary, an additional sample 94 requested of the patient before the test 86 is performed again. In a particular qualitative device it may not be necessary to take an additional sample 94. However, successive approximations using qualitative tests to acquire an approximate quantitative result may require that additional samples be taken from time to time. The computer 16 would alert the user 14 of the need to supply an additional sample. All such initial and additional samples would then be considered a single data acquisition event.

If the component is determined to be present at 88, or if the minimal setting LOD β has already been used, indicating that a component is not present within the limits of the detection device, it should be determined if this is the last component β for which a test is required. If it is not the last component, the test for the next component 98 would be initiated which may involve taking an additional sample 100. As with the quantitative test, however, it is also possible to simultaneously identify multiple components from a single sample or sample cycle. This is particularly the case for pattern recognition type technology, such as an electronic nose sensor array. Tunable diode lasers are also effective in identifying multiple components simultaneously. Thus, in addition to the diagnostic significance of a compound present in the breath, and the amount of compound present, the presence of the compound in a familiar pattern with other compounds may also be diagnostically significant.

After the qualitative components have been identified, it may be desirable to quantify certain of those components at step 102. Of course, only components determined to be present need be quantified. If no quantitative approximation is desired, the report 76 would again be generated. If a quantitative approximation is desired, it is determined whether a range 104 is requested or if a more narrow approximation is to be sought.

If a range is desired, a range test 80 is initiated, as shown in FIG. 3C. A first limit 106 for the particular patient is recalled from memory 22. This may involve setting the level of detection LOD to a particular level such that the component β will no longer be detected because the qualitative detector is no longer sensitive enough to recognize that component. This would indicate that the component is below a selected maximum. If necessary, a new sample is taken 108 and it is determined if the component β is present 110 at that level of detection LOD. If the component β is no longer detected, it would be reported 112 that the component falls below the selected limit. On the other hand, if the component continues to be detected, it would be reported that the component's concentration exceeds the selected limit 114. The data would be stored 116 indicating that for the particular component met or did not meet the selected criteria. This may be sufficient to determine if the component is low enough for health or if it exceeds a healthy range. If it is desired to place the component within a maximum and minimum range, a test for a second limit 118 should be performed. If the second limit test is performed, a new setting for the LOD is provided 120 and the cycle is repeated at the second selected setting. Results of the test are then delivered to the report section 76.

It may also be desired to obtain an approximation of the quantitative level for a particular component, employing a qualitative test device at subroutine 82, as shown in FIG. 3C. This may also be accomplished by adjusting the level of detection of the qualitative device and performing iterative tests. Because the patient's data is maintained over a longer period of time, the last level of detection for the component β can be recalled from memory at step 120. This provides a starting point for the search for the present level of the component. A new level of detection $LOD_{NEW}$ is obtained from the last level of detection plus or minus a selected a constant or "delta" 122. The $LOD_{NEW}$ must be lowered by taking new approximation 130 comprising $LOD_{LAST}$ plus the minimum $LOD_{MIN}$ divided by two. If it is determined 132 that the difference between $LOD_{NEW}$ and $LOD_{LAST}$ is less than a preselected limit, then the process should be halted as the desired degree of accuracy has been obtained. The information would then be stored 134 before. Otherwise, the microprocessor would repeat the process by applying $LOD_{NEW}$ to either an existing sample or a new sample 124.

We have described here one method for obtaining a quantitative approximation utilizing a qualitative device. Methods of numerical analysis known to persons skilled in the art will suggest other techniques that could be applied to obtain a similar result without departing from the teachings of our invention.

The results obtained from the quantitative tests 60, the presence test 78, range test 80 and qualitative approximation 82 are examined in the report algorithm 76 by the computer 16. Computer 16 should check for significant changes 136 in the selected components either α (quantitative) or β (qualitative) as set in a profile for the particular patient selected by the physician or as part of the step of identifying the selected tests 52. Significant deviations from the patient's chronic condition are reported both to the patient 138 and by the communications connection 26 through transmission 140 to the physician or healthcare provider. In addition significant components that exceed predetermined levels or are less than acceptable levels will be reported. Two-way communication across the information grid 26 would also permit the remote care-giver to select additional tests, initiate apparatus self-diagnostics, or perform other functions associated with setting or testing the apparatus from a remote location.

Maintaining the patient's chronic history of breath analysis enables our device to identify acute changes of significance to the patient's treatment and health. Background influences and variation from patient to patient can be reduced or eliminated by establishing this baseline condition for the patient. The tests described herein will be terminated 142 and may be performed again at a subsequent time thus allowing the patient to monitor his condition over time.

Significant changes in a patient's condition may be identified by suitable statistical or analytical methods. One such method for determining significant changes in multivariate data is described by Beebe et al., U.S. Pat. No. 5,592,402, incorporated herein by reference. Components of breath identified by the selected tests represent a multivariate data set that can be analyzed to determine whether abnormal features are present. Variations can be identified by establishing a calibration set from which a set of average values and expected statistical deviation from those values may be determined. Variations of a predetermined magnitude, for example more than three standard deviations from the expected average value, may be declared statistically significant and reported as such. Average values and statistical deviations may be set by providing an initial test period or series of initial samples taken under controlled conditions, or they may be continually updated by the apparatus either by calculating a cumulative average and deviation or by maintaining a rolling average and deviation. Moreover, the complex set of data may be separated into various sub-parts to further identify significant variation. Such sub-parts may include peak or minimum values, noise, baseline offset or baseline shape. Each of the sub-parts can be monitored to see if it is within the normal range expected for analysis. This may help in identifying which type of feature is abnormal. For example, different patients may have the same absolute value for a particular breath component. In one patient, this value may be associated with a with a particularly high baseline level. In another patient, the baseline may be rising sharply. In another, it may be falling slowly. In another, the value may have been reached by an acute change, exceeding a peak value and statistically significant. Yet another patient may routinely have much wider variation in the selected component and the change in value may not be statistically significant. For each patient, a different report may be provided, based on the learned pattern for the particular patient. Of course, absolute maximum or minimum values for given components may also be set, and measurements exceeding those maximum or minimum values may be reported without regard to patient history.

Figure 4:
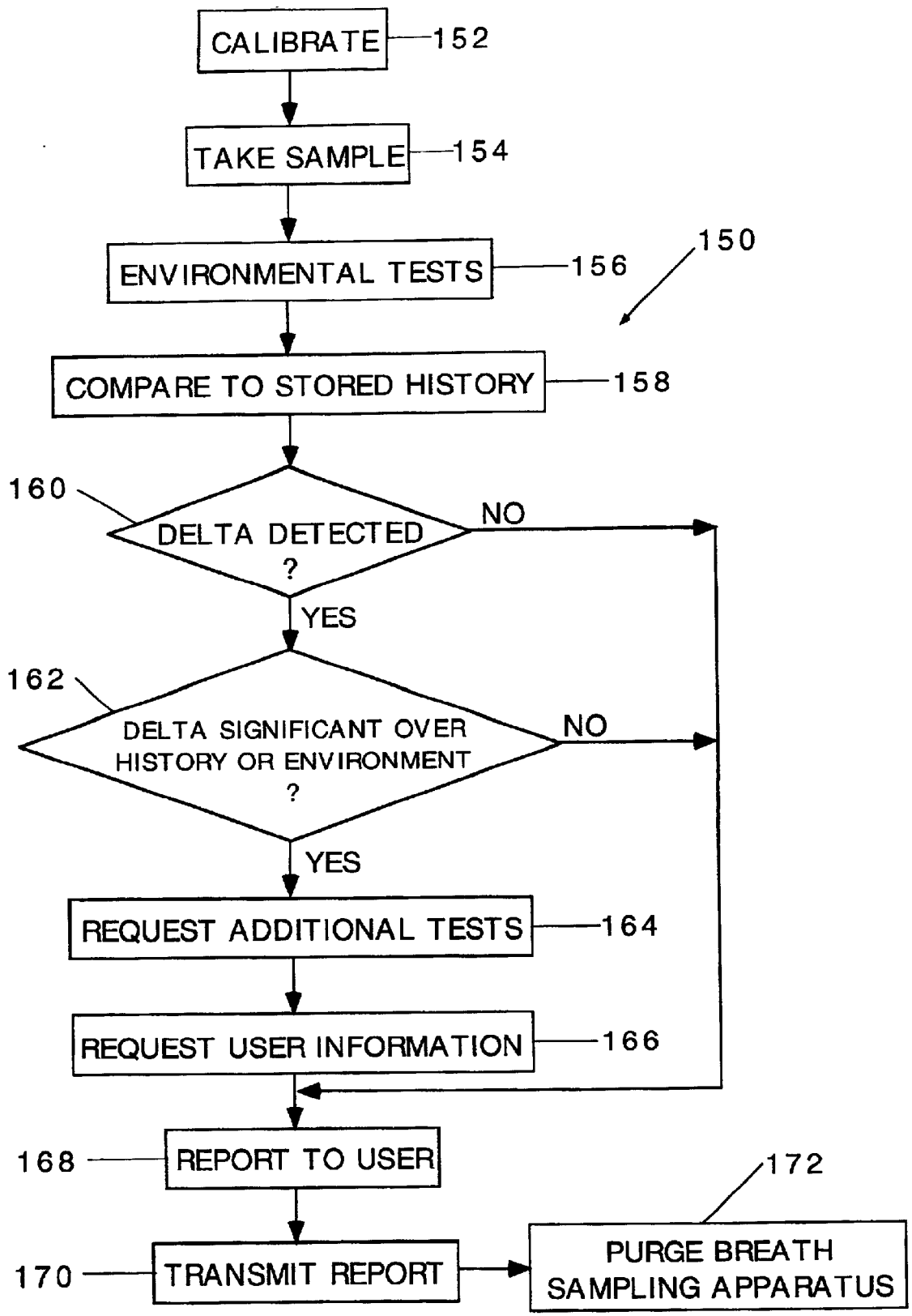
FIG. 4 is an additional flowchart including use of the system of FIG. 1.
Figure 5:
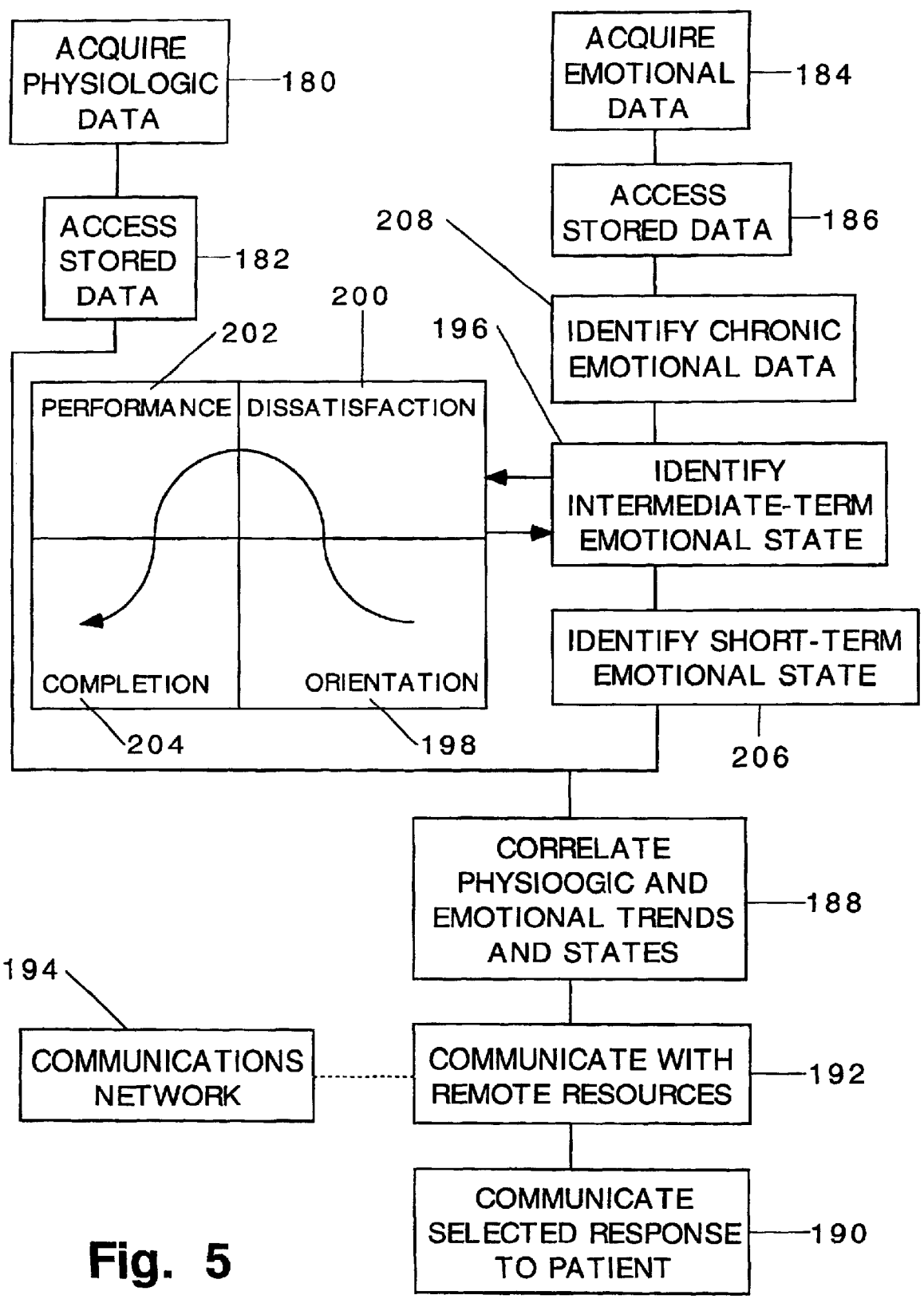
FIG. 5 is a functional diagram of a program for use with the system of FIG. 1.

The use of the breath analyzer 10 is further explained in connection with the flow chart 150 of FIG. 4. As shown in the flow chart 150, use of the breath analyzer 10 begins with calibration 152. This may be accomplished by injecting a gas of known composition into the device. A canister of such gas may be provided for this purpose. After calibration, a sample 154 is taken. This step includes the procedures described in greater detail above in connection with FIG. 3. The analyzer 10 may acquire environmental data at step 156, using the additional sensors 37 described above. The analyzer 10 would then compare 158 the stored history of the patent to present readings to determine 160 if a change has taken place. If there is a change, it is determined 162 if the change is significant in view of the patient's history and the environmental factors measured at step 156. If the change is determined to be significant, the analyzer may request additional tests 164. Such tests may include further breath tests for additional components not ordinarily in the set of tested components, repeat tests, or additional tests for which sensors 37 are provided, for example, blood pressure, blood oxygen (through, for example, an infrared sensor placed on the patient's finger), heart rate, weight, body fat composition, physical motion or body temperature. A cardiac pacemaker programming and data transfer wand may be one such sensor 37. Cardiac pacemakers often store historic data including numbers of pacing beats, number of ectopic beats, incidents of atrial fibrillation or tachyarrhythmia, or (for cardiovertor/defibrillators) ventricular fibrillation or tachyarrhythmia. Information on applied therapies, threshold levels, and even recorded electrocardiograms may be stored by a pacemaker or implantable cardiovertor/defibrillator. This information may be associated with the data records maintained by our device after transmission from the implanted cardiac stimulator. Techniques for such data transfer are well known.

The analyzer may also request the user or patient to enter certain data through the microcomputer user interface (e.g., keyboard or mouse). The requested data might include diet information, blood or urine levels of relevant analytes, perceived general state of health, amount and duration of recent exercise, weight, and similar factors which might either explain an acute change in breath components (that is, indicate that the change is not in fact significant) or provide important information for a health care provider.

After gathering additional information (steps 164 and 166) or if there was no change (step 160) or no significant change (step 162), a report will be generated 168 for the user and the information stored as part of the patient's history. The report or data may be transmitted 170 to a remote health care provider, either immediately or in response to a request for data. Finally, the system would be purged 172 to prevent contaminants from building up in the sampling device. As mentioned above, this may be accomplished by providing a gas of known composition and may be combined with the calibration step 172.

Multiple tests performed on a single sample may be independent or the results of several tests may be combined to produce a template or pattern representative of a patient's condition or representative of the presence of a particular compound or set of compounds. E-nose techniques have used pattern recognition to detect the presence of particular compounds. Multiple lasers could also be used on a single sample to extend the bandwidth for detection and pattern recognition could than be applied to the combined output of the several lasers. A single laser is generally capable of emitting light at certain limited frequencies. Although some tuning or variation of frequencies is possible, the elements or compounds that can be effectively recognized by a single laser device are limited by the frequency characteristics of the selected laser. The detector 34 of our invention may include multiple lasers, e.g. an array, having different emission frequencies. The lasers may be directed into a single sample by being physically offset around the sample, by being fired at slightly different times, or other techniques. Optical apparatus such as mirrors, lenses or prisms may be used to direct a beam from a selected laser along a path through the sample and into a detector. By adjusting the optical apparatus, beams from other lasers may be directed along the same or a similar path through the sample. By using lasers with different emission characteristics with the same sample, A wider set of data points may be obtained. Instead of three or four data points for a single laser, three lasers may obtain twelve or more data points from the same sample. This information may be expected to be both more selective and more quantitatively precise than similar information obtained by current electronic nose technology. The resulting more accurate information from all the laser beams can nevertheless be processed together, using pattern recognition methods in similar to those used in connection with e-nose techniques. As a result, a wider range of conditions or compounds may be identified by correlating the data pattern or changes in the data pattern over time. The above described array feature of e-nose technology can also be constructed with other analytical devices such as electrochemical, chemi-luminescence, microcoulometric, and fluorescence detectors.

In addition to measuring 180 a physiologic parameter correlated to a behavior or condition to be changed (for example, breath acetone as a marker for weight loss) and correlating stored patterns of that parameter 182, information 184 on the psychological or emotional state of the patient should be obtained. This information may be either directly obtained from the patient or may be inferred from the history 186 stored in the computer or both. To acquire information directly, the computer may pose a series of questions to the patient. The patient may be asked to indicate their perceived state on a scale, for instance. Preferably, the questions are changed from time to time, so that merely routine answers are less likely. Information on the patient's emotional or psychological state may also be inferred from the history maintained by the computer. For instance, early enthusiasm for a weight-loss program may be correlated with regular use of the breath analyzer to detect acetone, and a consistent pattern of acetone levels. Discouragement may be indicated by sporadic and increasingly infrequent use of the device, coupled with fluctuation of detected acetone levels including absence of acetone in the breath.

The physiologic parameter and the information on the psychological or emotional state of the patient are then correlated 188 to select an appropriate response or feedback for the patient 190. For example, adequate levels of acetone in the breath combined with a feeling of general satisfaction may produce a response merely acknowledging that the patient is in fact meeting his or her goals. Indications of discouragement coupled with adequate physiologic parameter may require more emphatic positive reinforcement to help the patient recognize that she is making progress. A depressed emotional state and poor physiologic measurements may require outside intervention. Intervention may include automatically alerting 192 a health care provider or a support person or support group so that personal contact may be made. A connection may be automatically initiated through a communications network 194, for example telephone or the Internet system, to the health care provider or support person, reporting the probable need for intervention.

The type of feedback provided to the patient may also depend on the patient's history as recorded by the computer. A process of changing a health-related activity or behavior may be viewed as a project or new job and is characterized by an emotional state which is related to the duration of the project, called herein an intermediate-term emotional state 196. Persons undertaking a project generally are observed to be in one of four states or conditions at different times during the project, each state needing a particular type of feed back. A successful project progresses through the four states. A particular patient may take more or less time in a particular state and may, at times, regress to an earlier state. The four states may be characterized as a beginning or orientation phase 198, a dissatisfaction phase 200, a production or performance phase 202 and a completion phase 204. As the project of changing behavior begins 198, the patient is usually enthusiastic, but has little real information relevant to the change in behavior. For example, the patient is excited about the prospect of improving healthy by weight loss, but doesn't know how to prepare appropriate meals in appropriate amounts. In general, specific, detailed direction is needed in this phase and the computer would provide detailed help. Health benefits are not yet apparent to the patient.

In the second phase 200, the health benefits have still not become obvious, and the patient may feel discouraged or dissatisfied. This phase needs feedback that is still detailed but which also includes positive re-enforcement to boost morale. In the case of weight loss, the detection of acetone components in the breath can provide immediate positive reenforcement necessary to help the patient through this phase.

In the third phase 202, physical changes begin to become apparent to the patient. The behavior can be seen to be having the desired effect. The patient's morale improves and feedback from the system should become less detailed but more supportive. In other words, the patient's range of choices increases as the patient becomes accustomed to the changed pattern of behavior. Positive re-enforcement is still needed.

In the final phase 204, the acquired pattern of behavior can be maintained indefinitely. The patient's morale and performance are both high. Detailed instructions are not needed and would not contribute to maintaining the desired behavior. Recognition and reward are needed to confirm the successful completion of the changed state. The patient maintains the new habits. In the case of weight loss, for example, acetone is a breath component only during weight loss, when the body is operating at an energy deficit. When the patient is maintaining a particular weight, measurable levels of acetone may not be detected.

The psychological pattern described above generally extends over the duration of an entire project. In the case of sustained weight loss, this period is usually about a year, comprised of six months of actual weight loss and six months of maintenance to allow the body to acclimate to the lower weight. Dieters and other persons trying to change a health-related behavior also experience wide emotional or psychological variation on a short-term basis 206. The person's need for re-enforcement and support may vary substantially throughout a single day. A recognized phenomenon in diabetics who are trying to lose weight is the tendency to over eat at the end of the day. Emotional states such as boredom, guilt (for eating "forbidden" foods), and lack of emotional support contribute to this phenomenon. By monitoring the patient's emotional state throughout the day, additional support or responses can be provided to help the patient cope with the short-term variations that can provide a significant barrier to successful behavior modification.

At the other end of the time spectrum, patients suffering from a chronic disease like diabetes or from gross obesity often also suffer from depression or other chronic emotional state 208. Clinical depression or similar chronic emotional state effects the emotional states of the patient observed over the intermediate term or duration of the project (e.g., diet) and on a daily or short-term basis. Factors contributing to the chronic emotional state of the patient may include family relationships, support groups and other friends, or the patient's acceptance or denial of their disease. These chronic emotional states may not be closely correlated to the time frame of project (diet) or to a daily or other repetitive cycle. A health care provider may prescribe intervention in the form of medication or therapy to help the patient. In any case, the existence of such a chronic emotional state must be taken into account when measuring either the daily or project-related status of the patient. The patient will develop a base line emotional state against which daily or longer-term changes can be detected. The feedback offered the patient preferably depends on a combination of all three emotional phases, that is, chronic (e.g., depression), intermediate (i.e., project related), and short-term (i.e., daily) variations, and on the detected physiologic parameter (e.g., breath acetone).

The patient needs to establish the new weight for an extended period. The system of detecting both a physiologic parameter and emotional or psychological state helps the patient make this transition to a maintenance diet by extending the transition period between weight loss and weight maintenance. Many patients view a diet as a temporary condition, to be endured only until the desired result has been achieved. For long-term weight maintenance, new habits must be established. This is particularly important for diabetics. Where either the beginning of the diet process is too abrupt (and lacking in observable results) or the end is too sudden (with a return to pre-diet practices), the patient's weight-loss program is likely to fail. By correlating both physiological parameters and emotional or psychological states, and providing feedback based on that correlation, both transitions can be made more gradual. The prospects of a long-term sustainable change of behavior are thereby enhanced.

What is claimed is:

1. A medical apparatus comprising:
    a breath-component analyzer, wherein said breath-component analyzer is a lipid degradation product analyzer for ketosis;
    a computer connected to said analyzer and receiving a breath-component signal from said analyzer;
    memory connected to said computer;
    a data structure stored in said memory representative of at least a first breath-component signal;
    a computer program comparing said stored data structure of said first breath-component signal;
    an input device recording information provided by the patient;
    a correlation program on said computer correlating input from said breath-component analyzer and input from said device and providing a response for said patient based on the correlating of said inputs; and
    a communications interface coupled to said computer, said interface communicating at least a portion of said response to said patient.

2. The medical apparatus of claim 1 further comprising a clock and wherein said data structure associates a time from said clock with said breath component signals.

3. The medical apparatus of claim 2 wherein said data structure stores a plurality of representations of breath content signals.

4. The medical apparatus of claim 3 wherein said computer program determines a rate of change of selected components of said breath component signal.

5. The medical apparatus of claim 1 wherein said breath-component analyzer is a quantitative analyzer.

6. The medical apparatus of claim 1 wherein said breath-component analyzer comprises a qualitative analyzer.

7. The medical apparatus of claim 6 further comprising a circuit iteratively measuring a component of breath to obtain an approximate quantitative measurement of said component.

8. The medical apparatus of claim 6 further comprising a circuit measuring a component of breath to obtain a range measurement of said component.

9. The medical apparatus of claim 1 further comprising a communications circuit for transmitting said comparison of said stored data structure and said breath component signal.

10. The medical apparatus of claim 1 wherein said computer program maintains a baseline representation of a chronic condition of a patient's breath components and identifies significant acute deviations from said baseline representation.

11. The medical apparatus of claim 1 wherein said computer program stores a plurality of data structures and associates said data structures with a single patient.

12. The medical apparatus of claim 1 further comprising at least one environmental sensor producing an output and wherein said data structure includes a representation of said output, said representation being associated with said breath-component signal.

13. The medical apparatus of claim 12 wherein said environmental sensor includes at least one of a thermometer, a hygrometer or a barometer.

14. The medical apparatus of claim 1 further comprising at least one patient condition sensor producing a patient condition output and wherein said data structure includes a representation of said patient condition output, said representation being associated with said breath-component signal.

15. The medical apparatus of claim 14 wherein said patient condition sensor comprises at least one of a weight scale, a thermometer, a blood-oxygen content sensor, a blood pressure sensor, a cardiac pulse sensor, or an implantable cardiac stimulator data transfer device.

16. The medical apparatus of claim 1 further comprising means for comparing said stored data structure with said breath-component signal, means for detecting a change between said stored data structure and said breath component signal, and means for requesting additional input in response to said detected change.

17. The medical apparatus of claim 16 wherein said means for requesting additional input comprises at least one patient condition sensor producing a patient condition output and wherein said data structure includes a representation of said patient condition output, said representation being associated with said breath-component signal.

18. The medical apparatus of claim 17 wherein said patient condition sensor comprises at least one of a weight scale, a thermometer, a blood-oxygen content sensor, a blood pressure sensor, a cardiac pulse sensor, or an implantable cardiac stimulator data transfer device.

19. The medical apparatus of claim 17 wherein said means for requesting additional input includes a computer user interface.

20. The medical apparatus of claim 16 wherein said means for requesting additional input includes a computer user interface.

21. The medical apparatus of claim 1 wherein said breath component analyzer comprises at least one laser spectrometer having a plurality of lasers, at least one of said lasers emitting radiation at wavelengths different from wavelengths emitted by another of said lasers.

22. The medical apparatus of claim 21 further comprising pattern recognition apparatus in communication with said spectrometer having a plurality of lasers, said pattern recognition apparatus correlating data from said plurality of lasers.

23. The medical apparatus of claim 1 further comprising
an input device recording information provided by the patient,
a correlation program on said computer correlating input from said breath-component analyzer and input from said device and providing a response for said patient based on the correlating of said inputs, and
a communications interface coupled to said computer, said interface communicating at least a portion of said response to said patient.

24. The apparatus of claim 23 further comprising a connection to a communication network.

25. A medical apparatus comprising:
a breath-component analyzer, wherein said breath-component analyzer is an acetone analyzer for detecting weight loss;
a computer connected to said analyzer and receiving a breath-component signal from said analyzer;
memory connected to said computer;
a data structure stored in said memory representative of at least a first breath-component signal;
a computer program comparing said stored data structure of said first breath-component signal;
an input device recording information provided by the patient;
a correlation program on said computer correlating input from said breath-component analyzer and input from said device and providing a response for said patient based on the correlating of said inputs; and
a communications interface coupled to said computer, said interface communicating at least a portion of said response to said patient.

26. The medical apparatus of claim 25 wherein information provided by the patient includes information related to the emotional/psychological state of the patient.

27. The medical apparatus of claim 26 wherein said correlation program identifies a chronic emotional state of a patient.

28. The medical apparatus of claim 26 wherein said correlation program identifies an intermediate-term emotional state of a patient.

29. The medical apparatus of claim 26 wherein said correlation program identifies a short-term emotional state of said patient.

30. The medical apparatus of claim 25 wherein said correlation program identifies a chronic emotional state of said patient, an intermediate-term emotional state of said patient, and a short-term emotional state of said patient, and correlates the chronic, intermediate-term and short-term emotional states of said patient with said input from said breath analyzer.

31. A method for analyzing breath of a patient for at least one component comprising acetone, comprising the steps of taking a breath sample from a patient;
analyzing components of said sample to product a first breath component profile;
storing said first breath component profile in computer-accessible memory;
taking a second breath sample from said patient;
analyzing components of said sample to produce a second breath component profile;
comparing said first and second breath component profiles;
recording information provided by the patient through an input device;
correlating in a computer, input from said breath-component analyzer and input from said device; and
providing a response for said patient based on said inputs.

32. The method of claim 31 further comprising associating a time from a clock with said breath component signals.

33. The method of claim 32 further comprising storing a plurality of representations of breath content signals acquired at a plurality of times.

34. The method of claim 33 further comprising determining a rate of change of selected components of said breath component signal between said plurality of representations.

35. The method of claim 31 further comprising quantitatively analyzing breath components.

36. The method of claim 31 further comprising qualitatively analyzing breath components.

37. The method of claim 36 further comprising iteratively qualitatively analyzing a component of breath at selected sensitivities to obtain an approximate quantitative measurement of said component.

38. The method of claim 36 further comprising measuring a component of breath to obtain a range measurement of said component.

39. The method of claim 31 further comprising transmitting said comparison of said stored data structure and said breath component signal.

40. The method of claim 31 further comprising maintaining a baseline representation of a chronic condition of a patient's breath components and identifying significant acute deviations from said baseline representation.

41. The method of claim 31 further comprising storing a plurality of data structures and associating said data structures with a single patient.

42. The method of claim 31 further comprising sensing at least one environmental condition at the time of taking a breath sample, storing a representation of said sensed condition in computer-accessible memory, and associating said representation with the breath-component profile produced from said breath sample.

43. The method of claim 42 wherein said sensing at least one environmental condition includes at least one of temperature, humidity or barometric pressure.

44. The method of claim 31 further comprising sensing at least one patient condition at the time of taking a breath sample, storing a representation of said sensed patient condition in computer-accessible memory, and associating said representation with the breath-component profile produced from said breath sample.

45. The method of claim 44 wherein said sensing at least one patient condition comprises at least one of body weight, body temperature, blood-oxygen content, blood pressure, pulse rate, or data recorded by an implantable cardiac stimulator.

46. The method of claim 31 further detecting a change between said stored breath component profile and said second breath component profile, and requesting additional input in response to said detected change.

47. The method of claim 46 wherein requesting additional input comprises sensing at least one patient condition, storing a representation of said sensed patient condition in computer-accessible memory, and associating said representation with the breath-component profile produced from said breath sample.

48. The method of claim 47 wherein said sensing at least one patient condition comprises at least one of body weight, body temperature, blood-oxygen content, blood pressure, pulse rate, or data recorded by an implantable cardiac stimulator.

49. The method of claim 47 wherein requesting additional input includes requesting and receiving information through a computer-user interface.

50. The method of claim 46 wherein requesting additional input includes requesting and receiving information through a computer-user interface.

51. The method of claim 31 wherein said steps of analyzing breath components comprise passing a plurality of lasers beams through said breath sample, at least one of said lasers beams having wavelengths different from wavelengths of another of said laser beams and spectrally analyzing said laser beams after said beams have passed through said sample.

52. The method of claim 51 wherein said step of spectrally analyzing said laser beams further comprises pattern recognition processing.

53. The method of claim 52 further comprising connecting to a communication network.

54. The method of claim 53 wherein information provided by the patient includes information related to the emotional/psychological state of the patient.

55. The method of claim 54 wherein correlating input includes identifying a chronic emotional state of a patient.

56. The method of claim 54 wherein correlating input includes identifying an intermediate-term emotional state of a patient.

57. The method of claim 54 wherein correlating input includes identifying a short-term emotional state of said patient.

58. The method of claim 52 wherein correlating input includes identifying a chronic emotional state of said patient, an intermediate-term emotional state of said patient, and a short-term emotional state of said patient, and correlating the chronic, intermediate-term and short-term emotional states of said patient with said input from said breath analyzer.

* * * * *